US011504007B2

United States Patent
Yamamoto et al.

(10) Patent No.: US 11,504,007 B2
(45) Date of Patent: *Nov. 22, 2022

(54) PHOTOACOUSTIC IMAGE GENERATION APPARATUS

(71) Applicant: FUJIFILM Corporation, Tokyo (JP)

(72) Inventors: Katsuya Yamamoto, Kanagawa (JP); Kaku Irisawa, Kanagawa (JP); Dai Murakoshi, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 734 days.

This patent is subject to a terminal disclaimer.

(21) Appl. No.: 16/357,036

(22) Filed: Mar. 18, 2019

(65) Prior Publication Data
US 2019/0209018 A1 Jul. 11, 2019

Related U.S. Application Data

(63) Continuation of application No. PCT/JP2017/033344, filed on Sep. 14, 2017.

(30) Foreign Application Priority Data
Sep. 21, 2016 (JP) .............................. JP2016-183786

(51) Int. Cl.
*A61B 5/00* (2006.01)
*A61B 17/34* (2006.01)
(Continued)

(52) U.S. Cl.
CPC .......... *A61B 5/0095* (2013.01); *A61B 5/6848* (2013.01); *A61B 8/06* (2013.01);
(Continued)

(58) Field of Classification Search
CPC ....... A61B 5/0095; A61B 5/6848; A61B 8/13; A61B 8/06; A61B 8/0841; A61B 8/4416;
(Continued)

(56) References Cited

U.S. PATENT DOCUMENTS

2006/0247521 A1* 11/2006 McGee ................ A61B 5/0071
600/434
2012/0078103 A1* 3/2012 Tashiro .................... A61B 8/54
600/443
(Continued)

FOREIGN PATENT DOCUMENTS

JP 2009-207588 A 9/2009
JP 4594675 B2 * 12/2010 ............... A61B 8/00
(Continued)

OTHER PUBLICATIONS

Extended European Search Report for European Application No. 17852960.8, dated Sep. 2, 2019.
(Continued)

*Primary Examiner* — Sean D Mattson
(74) *Attorney, Agent, or Firm* — Birch, Stewart, Kolasch & Birch, LLP

(57) ABSTRACT

A photoacoustic image generation apparatus includes: a puncture needle that generates photoacoustic waves; an ultrasound probe that detects the photoacoustic waves and reflected ultrasonic waves reflected by the transmission of ultrasonic waves; a processor that generates a color Doppler signal of a region of interest as a color Doppler measurement target, generates a photoacoustic image on the basis of the photoacoustic waves, and detects the position of a tip portion of the puncture needle on the basis of the photoacoustic image; and a controller that sets the region of interest such that the position of the tip portion of the puncture needle and a center position of the region of interest are separated from each other by a predetermined distance and sets the region of interest, following the movement of the tip portion of the puncture needle, in a state in which the distance is maintained.

13 Claims, 11 Drawing Sheets

(51) Int. Cl.
- *A61B 8/13* (2006.01)
- *A61B 8/06* (2006.01)
- *A61B 8/08* (2006.01)
- *A61B 8/00* (2006.01)
- *A61B 90/30* (2016.01)

(52) U.S. Cl.
CPC .............. *A61B 8/0841* (2013.01); *A61B 8/13* (2013.01); *A61B 8/4416* (2013.01); *A61B 8/488* (2013.01); *A61B 17/3403* (2013.01); *A61B 2090/306* (2016.02); *A61B 2576/00* (2013.01)

(58) Field of Classification Search
CPC ................ A61B 8/488; A61B 17/3403; A61B 2090/306; A61B 2576/00
See application file for complete search history.

(56) References Cited

U.S. PATENT DOCUMENTS

| | | | | |
|---|---|---|---|---|
| 2013/0096430 | A1* | 4/2013 | Yoshiara | A61B 8/463 600/438 |
| 2014/0180135 | A1 | 6/2014 | Hoseit et al. | |
| 2014/0296694 | A1* | 10/2014 | Jaworski | A61B 8/463 600/409 |
| 2015/0297092 | A1* | 10/2015 | Irisawa | A61B 17/3403 600/407 |
| 2015/0342561 | A1* | 12/2015 | Takeda | A61B 17/3403 600/424 |
| 2016/0151039 | A1* | 6/2016 | Morikawa | A61B 8/06 600/424 |
| 2019/0216425 | A1* | 7/2019 | Yamamoto | A61B 8/06 |

FOREIGN PATENT DOCUMENTS

| | | | |
|---|---|---|---|
| JP | 2013-5957 A | 1/2013 | |
| JP | 2013-81764 A | 5/2013 | |
| JP | 2014-136102 A | 7/2014 | |
| JP | 2015-231583 A | 12/2015 | |
| WO | WO-2014109148 A1 * | 7/2014 | .............. A61B 90/13 |
| WO | WO 2016/040383 A1 | 3/2016 | |

OTHER PUBLICATIONS

Piras et al, "Photoacoustic needle: minimally invasive guidance to biopsy," Journal of Biomedical Optics, vol. 18, No. 7, Jul. 2013, pp. 070502-1 to 070502-3 (4 pages total).

Japanese Office Action for Japanese Application No. 2018-541025, dated Mar. 17, 2020, with an English translation.

International Preliminary Report on Patentability and Written Opinion of the International Searching Authority for International Application No. PCT/2017/033344, dated Apr. 4, 2019, with English translation.

International Search Report for International Application No. PCT/JP2017/033344, dated Oct. 10, 2017, with English translation.

Japanese Office Action, dated Dec. 10, 2019, for Japanese Application No. 2018-541025, with an English translation.

Office Action for European Application No. 17852960.8, dated Jul. 7, 2022.

* cited by examiner

FIG. 12

| FRAME NUMBER | 1 | 2 | 3 | 4 | 5 | 6 | 7 | 8 | 9 | 10 | 11 | 12 | 13 | 14 | 15 | 16 | 17 | 18 | 19 | 20 |
|---|---|---|---|---|---|---|---|---|---|---|---|---|---|---|---|---|---|---|---|---|
| DETECTION PROCESS ON/OFF | ON | ON | OFF | ON | OFF | OFF | ON | OFF | OFF | OFF | ON | ON | ON | ON | OFF | ON | OFF | OFF | ON | OFF |
| ANGLE OF TRAVELING DIRECTION OF PUNCTURE NEEDLE | 30° | 30° | - | 30° | - | - | 30° | - | - | - | 45° | 20° | 15° | 15° | - | 15° | - | - | 15° | - |

PHOTOACOUSTIC IMAGE GENERATION APPARATUS

CROSS-REFERENCE TO RELATED APPLICATIONS

This application is a continuation application of International Application No. PCT/JP2017/033344, filed Sep. 14, 2017, the disclosure of which is incorporated herein by reference in its entirety. Further, this application claims priority from Japanese Patent Application No. 2016-183786, filed Sep. 21, 2016, the disclosure of which is incorporated herein by reference in its entirety.

BACKGROUND

1. Technical Field

The present invention relates to a photoacoustic image generation apparatus comprising an insert of which at least a portion is inserted into a subject and which includes a photoacoustic wave generation portion that absorbs light and generates photoacoustic waves.

2. Related Art

An ultrasonography method has been known as a kind of image inspection method that can non-invasively inspect the internal state of a living body. In ultrasonography, an ultrasound probe that can transmit and receive ultrasonic waves is used. In a case in which the ultrasound probe transmits ultrasonic waves to a subject (living body), the ultrasonic waves travel in the living body and are reflected from the interface between tissues. The ultrasound probe receives the reflected ultrasonic waves and a distance is calculated on the basis of the time until the reflected ultrasonic waves return to the ultrasound probe. In this way, it is possible to capture an image indicating the internal aspect of the living body.

In addition, photoacoustic imaging has been known which captures the image of the inside of a living body using a photoacoustic effect. In general, in the photoacoustic imaging, the inside of the living body is irradiated with pulsed laser light. In the inside of the living body, a living body tissue absorbs the energy of the pulsed laser light and ultrasonic waves (photoacoustic waves) are generated by adiabatic expansion caused by the energy. For example, an ultrasound probe detects the photoacoustic waves and a photoacoustic image is formed on the basis of a detection signal. In this way, it is possible to visualize the inside of the living body on the basis of the photoacoustic waves.

In addition, as a technique related to the photoacoustic imaging, JP2015-231583A discloses a puncture needle in which a photoacoustic wave generation portion that absorbs light and generates photoacoustic waves is provided in the vicinity of a tip. In the puncture needle, an optical fiber is provided up to the tip of the puncture needle and light guided by the optical fiber is emitted to the photoacoustic wave generation portion. An ultrasound probe detects the photoacoustic waves generated by the photoacoustic wave generation portion and a photoacoustic image is generated on the basis of a detection signal of the photoacoustic waves. In the photoacoustic image, a part of the photoacoustic wave generation portion appears as a bight point, which makes it possible to check the position of the puncture needle using the photoacoustic image.

In addition, Doppler measurement has been known as a kind of ultrasonography. The Doppler measurement is a measurement method that non-invasively measures, for example, hemodynamics, a blood flow rate, and trends in vivo on the basis of the Doppler shift of the frequency of received waves with respect to the frequency of transmitted waves. Examples of the Doppler measurement include pulsed Doppler measurement which transmits pulsed ultrasonic waves, detects reflected ultrasonic waves, analyzes the Doppler shift of the reflected ultrasonic waves, and displays a waveform and color Doppler measurement which maps the distribution of a blood flow rate and displays a color Doppler image. For example, JP2009-207588A discloses a technique that detects the tip of a puncture needle in an ultrasound image and sets a sample gate as a pulsed Doppler measurement target in the vicinity of the tip, in order to easily check a blood flow on a puncture needle guide in a case in which pulsed Doppler measurement is performed while the puncture needle is being used.

SUMMARY

Here, it is considered that the puncture needle generating photoacoustic waves disclosed in JP2015-231583A is used in order to check the position of the tip of the puncture needle in a case in which ultrasonography using the puncture needle is performed.

However, in a case in which color Doppler measurement is performed using the puncture needle generating photoacoustic waves disclosed in JP2015-231583A, a color Doppler signal obtained by the color Doppler measurement is a weak signal. Therefore, in a case in which the positional relationship between the tip of the puncture needle and a region of interest which is a color Doppler measurement target is not appropriately set, a signal caused by the reflected waves of the ultrasonic waves from the puncture needle is included as an artifact in the color Doppler signal obtained by the color Doppler measurement, which makes it difficult to acquire an accurate color Doppler signal.

In addition, JP2009-207588A does not disclose any technique considering the influence of the reflected waves from the puncture needle in a case in which a region of interest is set in the color Doppler measurement.

The invention has been made in view of the abovementioned problems and an object of the invention is to provide a photoacoustic image generation apparatus that can suppress the generation of an artifact caused by reflected waves from an insert, such as a puncture needle that generates photoacoustic waves from a tip, in a case in which color Doppler measurement is performed with the insert.

A photoacoustic image generation apparatus according to the invention comprises: an insert of which at least a tip portion is inserted into a subject and which includes a light guide member that guides light to the tip portion and a photoacoustic wave generation portion that absorbs the light guided by the light guide member and generates photoacoustic waves; an acoustic wave detection unit that detects the photoacoustic waves generated from the photoacoustic wave generation portion and detects reflected acoustic waves reflected by transmission of acoustic waves to the subject; a color Doppler signal generation unit that generates a color Doppler signal on the basis of the reflected acoustic waves in a region of interest as a color Doppler measurement target which have been detected by the acoustic wave detection unit; a photoacoustic image generation unit that generates a photoacoustic image on the basis of the photoacoustic waves detected by the acoustic wave detection unit; a tip position detection unit that detects a position of the tip portion of the insert on the basis of the photoacoustic image;

and a control unit that sets the region of interest such that the position of the tip portion of the insert detected by the tip position detection unit and a center position of the region of interest are separated from each other by a predetermined distance and sets the region of interest, following movement of the tip portion of the insert, in a state in which the distance is maintained.

In the photoacoustic image generation apparatus according to the invention, in a case in which an orientation direction is a left-right direction, the control unit may set the region of interest such that the tip of the insert is included in a predetermined range in the left-right direction from a position of one end, which is closer to the tip portion of the insert, of left and right ends of the region of interest having a rectangular shape.

In the photoacoustic image generation apparatus according to the invention, a plurality of detection elements that detect the reflected acoustic waves and the photoacoustic waves may be arranged in the acoustic wave detection unit and the control unit may set the region of interest such that the tip of the insert is included in a range of a length of one detection element in the left-right direction from the position of the one end of the region of interest which is closer to the tip portion of the insert as a center line.

In the photoacoustic image generation apparatus according to the invention, the control unit may set the region of interest such that the tip of the insert is included in a range of a length which is 5% of a length of the region of interest in the orientation direction from the position of the one end of the region of interest which is closer to the tip portion of the insert as a center line.

In the photoacoustic image generation apparatus according to the invention, the control unit may set the region of interest such that the position of the one end of the region of interest which is closer to the tip portion of the insert in the left-right direction is matched with a position of the tip of the insert in the left-right direction.

The photoacoustic image generation apparatus according to the invention may further comprise: a reflected acoustic image generation unit that generates a reflected acoustic image on the basis of the reflected acoustic waves; and an insert detection unit that detects a length direction of the insert on the basis of the reflected acoustic image. The control unit may set the region of interest such that a center line of the region of interest in the orientation direction and a straight line extending in the length direction of the insert intersect each other in the region of interest.

In the photoacoustic image generation apparatus according to the invention, the control unit may set the region of interest such that the center line of the region of interest in the orientation direction and the straight line extending in the length direction of the insert intersect each other in a predetermined range from a center of the region of interest in a depth direction.

In the photoacoustic image generation apparatus according to the invention, the control unit may set the region of interest such that the straight line extending in the length direction of the insert intersects the center position of the region of interest.

In the photoacoustic image generation apparatus according to the invention, the insert detection unit may detect the length direction of the insert at each interval of two or more frames of the reflected acoustic images.

In the photoacoustic image generation apparatus according to the invention, the insert detection unit may acquire an amount of change in an angle of the length direction of the insert and increase the frame interval at which the length direction of the insert is detected in a case in which the amount of change is equal to or less than a predetermined threshold value.

In the photoacoustic image generation apparatus according to the invention, in a case in which the position of the tip portion of the insert detected by the tip position detection unit is the same as a position of the tip portion of the insert in the photoacoustic image of a previous frame, the detection of the insert based on the reflected acoustic image and the setting of the region of interest based on the position of the tip portion of the insert may not be performed.

In the photoacoustic image generation apparatus according to the invention, in a case in which a side of the subject which is close to the acoustic wave detection unit in a depth direction is an upper side, the control unit may set the region of interest such that an upper end of the region of interest having the rectangular shape is lower than the position of the tip of the insert.

In the photoacoustic image generation apparatus according to the invention, in a case in which a side of the subject which is close to the acoustic wave detection unit in a depth direction is an upper side, the control unit may set the region of interest such that the tip of the insert is included in a predetermined range in an upper direction and a lower direction from a position of an upper end of the region of interest having the rectangular shape.

In the photoacoustic image generation apparatus according to the invention, the control unit may set the region of interest such that the tip of the insert is included in a range of a length, which is 5% of a length of the region of interest in the depth direction, in each of the upper direction and the lower direction from the position of the upper end of the region of interest as a center line.

In the photoacoustic image generation apparatus according to the invention, in a case in which a side of the subject which is close to the acoustic wave detection unit in a depth direction is an upper side, the control unit may set the region of interest such that a position of an upper end of the region of interest in an up-down direction is matched with the position of the tip of the insert in the up-down direction.

In the photoacoustic image generation apparatus according to the invention, preferably, the insert is a needle that is inserted into the subject.

The photoacoustic image generation apparatus according to the invention generates a photoacoustic image on the basis of the detection signal of the photoacoustic waves generated from the photoacoustic wave generation portion of the insert, detects the position of the tip portion of the insert on the basis of the photoacoustic image, sets a region of interest as a color Doppler measurement target such that the detected position of the tip portion of the insert and the center position of the region of interest as the color Doppler measurement target are separated from each other by a predetermined distance, and sets the region of interest, following the movement of the tip portion of the insert, in a state in which the distance is maintained. Therefore, it is possible to suppress the generation of an artifact caused by the reflected waves from the insert.

BRIEF DESCRIPTION OF THE DRAWINGS

Exemplary embodiments according to the technique of the present disclosure will be described in detail based on the following figures, wherein:

FIG. 12 is a diagram illustrating a method for controlling the turn-on and turn-off of a process of detecting a length direction of the puncture needle on the basis of the amount of change in the angle of the length direction of the puncture needle.

DETAILED DESCRIPTION

Figure 1:
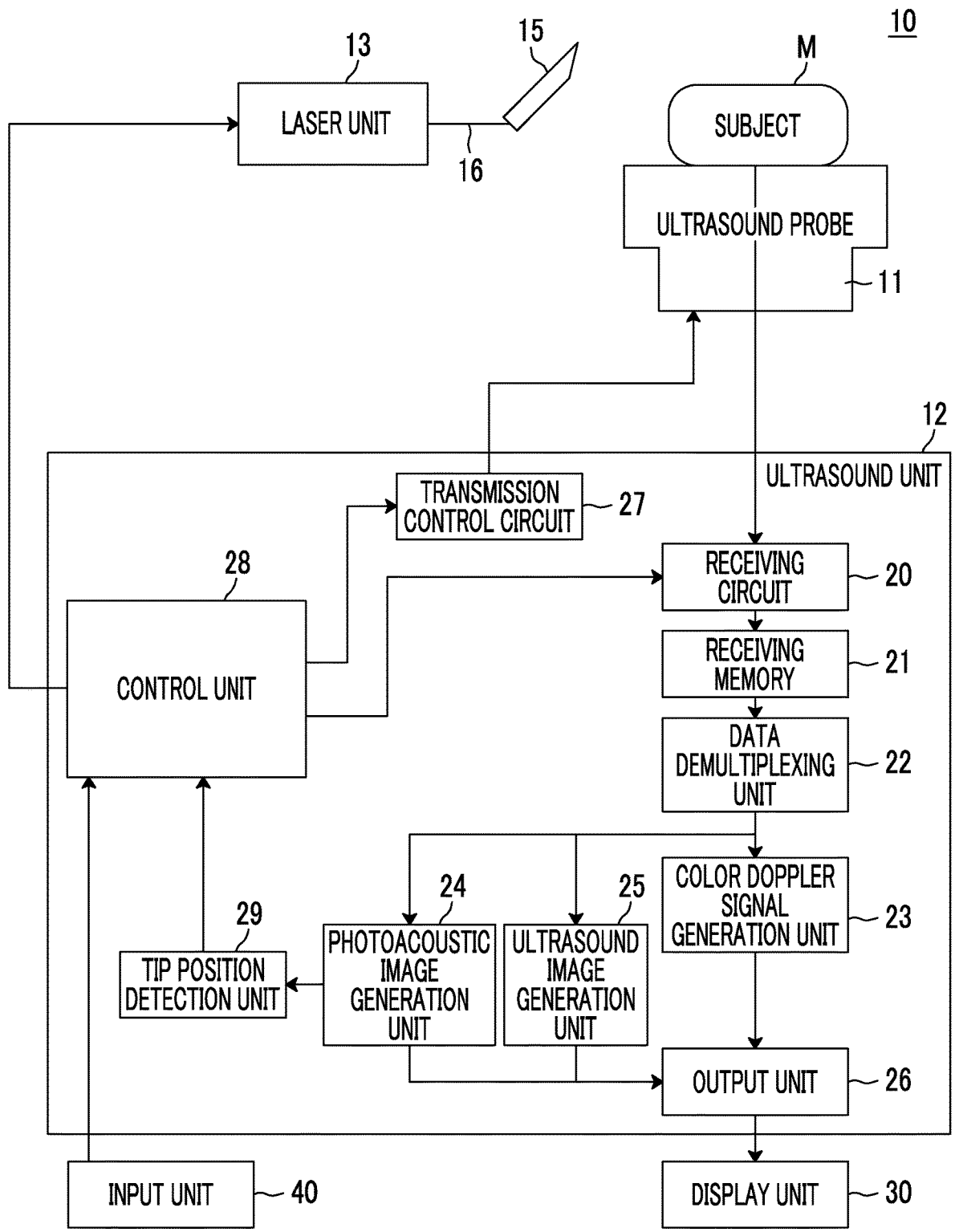
FIG. 1 is a block diagram schematically illustrating the configuration of a first embodiment of a photoacoustic image generation apparatus according to the invention.

Hereinafter, a first embodiment of a photoacoustic image generation apparatus according to the invention will be described in detail with reference to the drawings. FIG. 1 is a diagram schematically illustrating the configuration of a photoacoustic image generation apparatus 10 according to this embodiment.

As illustrated in FIG. 1, the photoacoustic image generation apparatus 10 according to this embodiment comprises an ultrasound probe 11, an ultrasound unit 12, a laser unit 13, and a puncture needle 15. The puncture needle 15 and the laser unit 13 are connected by an optical cable 16 having an optical fiber. The puncture needle 15 can be attached to and detached from the optical cable 16 and is disposable. In addition, in this embodiment, ultrasonic waves are used as acoustic waves. However, the invention is not limited to the ultrasonic waves. Acoustic waves with an audible frequency may be used as long as an appropriate frequency can be selected according to, for example, an inspection target or measurement conditions.

The laser unit 13 comprises a solid-state laser light source using, for example, yttrium aluminum garnet (YAG) and alexandrite. Laser light emitted from the solid-state laser light source of the laser unit 13 is guided by the optical cable 16 and is incident on the puncture needle 15. The laser unit 13 according to this embodiment emits pulsed laser light in a near-infrared wavelength range. The near-infrared wavelength range means a wavelength range from about 700 nm to 850 nm. In this embodiment, the solid-state laser light source is used. However, other laser light sources, such as a gas laser light source, may be used or light sources other than the laser light source may be used.

Figure 2:
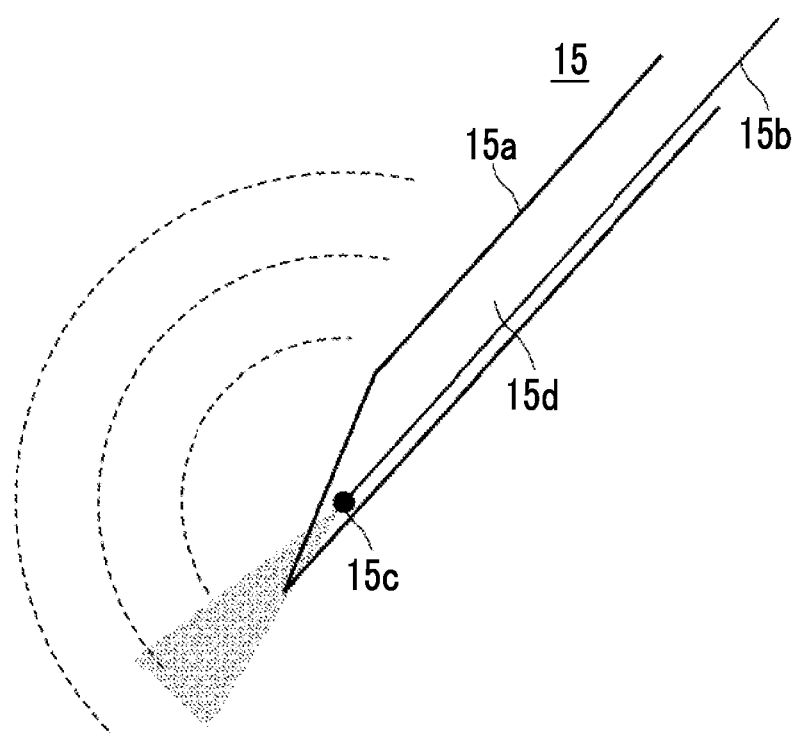
FIG. 2 is a cross-sectional view illustrating the configuration of a tip portion of a puncture needle.

The puncture needle 15 is an embodiment of an insert according to the invention and is a needle that is inserted into a subject M. FIG. 2 is a cross-sectional view including a center axis that extends in a length direction of the puncture needle 15. The puncture needle 15 includes a puncture needle main body 15a that has an opening at an acute tip and is formed in a hollow shape, an optical fiber 15b (corresponding to a light guide member according to the invention) that guides laser light emitted from the laser unit 13 to the vicinity of the opening of the puncture needle 15, and a photoacoustic wave generation portion 15c that absorbs laser light emitted from the optical fiber 15b and generates photoacoustic waves.

The optical fiber 15b and the photoacoustic wave generation portion 15c are provided in a hollow portion 15d of the puncture needle main body 15a. For example, the optical fiber 15b is connected to the optical fiber in the optical cable 16 (see FIG. 1) through an optical connector that is provided at the base end of the puncture needle 15. For example, a laser light of 0.2 mJ is emitted from a light emission end of the optical fiber 15b.

The photoacoustic wave generation portion 15c is provided at the light emission end of the optical fiber 15b and is provided in the vicinity of the tip of the puncture needle 15 and in the inner wall of the puncture needle main body 15a. The photoacoustic wave generation portion 15c absorbs the laser light emitted from the optical fiber 15b and generates photoacoustic waves. The photoacoustic wave generation portion 15c is made of, for example, an epoxy resin, a polyurethane resin, a fluorine resin, and silicone rubber with which a black pigment is mixed. In FIG. 2, the photoacoustic wave generation portion 15c is illustrated to be larger than the optical fiber 15b. However, the invention is not limited thereto. The photoacoustic wave generation portion 15c may have a size that is equal to the diameter of the optical fiber 15b.

The photoacoustic wave generation portion 15c is not limited to the above and a metal film or an oxide film having light absorptivity with respect to the wavelength of laser light may be used as the photoacoustic wave generation portion. An oxide film made of, for example, iron oxide, chromium oxide, or manganese oxide having high light absorptivity with respect to the wavelength of laser light can be used as the photoacoustic wave generation portion 15c. Alternatively, a metal film made of, for example, titanium (Ti) or platinum (Pt) that has a lower light absorptivity than an oxide and has a higher biocompatibility than an oxide may be used as the photoacoustic wave generation portion 15c. In addition, the position where the photoacoustic wave generation portion 15c is provided is not limited to the inner wall of the puncture needle main body 15a. For example, a metal film or an oxide film which is the photoacoustic wave generation portion 15c may be formed on the light emission end of the optical fiber 15b with a thickness of about 100 nm by vapor deposition such that the oxide film covers the light emission end. In this case, at least a portion of the laser light emitted from the light emission end of the optical fiber 15b is absorbed by the metal film or the oxide film covering the light emission end and photoacoustic waves are generated from the metal film or the oxide film.

The vicinity of the tip of the puncture needle 15 means a position where the photoacoustic wave generation portion 15c can generate photoacoustic waves capable of imaging the position of the tip of the puncture needle 15 with accuracy required for a needling operation in a case in which the tip of the optical fiber 15b and the photoacoustic wave generation portion 15c are disposed at the position. For example, the vicinity of the tip of the puncture needle 15 is the range of 0 mm to 3 mm from the tip to the base end of the puncture needle 15. In the subsequent embodiments, the meaning of the vicinity of the tip is the same as described above.

Returning to FIG. 1, the ultrasound probe 11 corresponds to an acoustic wave detection unit according to the invention and includes, for example, a plurality of ultrasound transducers which are one-dimensionally arranged. The ultrasound transducer is, for example, a piezoelectric element made of a polymer film, such as piezoelectric ceramics or polyvinylidene fluoride (PVDF).

The ultrasound probe 11 detects the photoacoustic waves generated from the photoacoustic wave generation portion 15c after the puncture needle 15 is inserted into a subject M. In addition, the ultrasound probe 11 performs the transmission of acoustic waves (ultrasonic waves) to the subject M and the detection of reflected acoustic waves (reflected ultrasonic waves) with respect to the transmitted ultrasonic waves, in addition to the detection of the photoacoustic waves. In a case in which Doppler measurement is performed, the ultrasound probe 11 transmits pulsed ultrasonic waves and detects reflected ultrasonic waves with respect to the pulsed ultrasonic waves. In addition, the transmission and reception of the ultrasonic waves may be performed at different positions. For example, ultrasonic waves may be transmitted from a position different from the position of the ultrasound probe 11 and the ultrasound probe 11 may receive the reflected ultrasonic waves with respect to the transmitted ultrasonic waves. For example, a linear ultrasound probe, a convex ultrasound probe, or a sector ultrasound probe may be used as the ultrasound probe 11.

The ultrasound unit 12 includes the receiving circuit 20, a receiving memory 21, a data demultiplexing unit 22, a color Doppler signal generation unit 23, a photoacoustic image generation unit 24, an ultrasound image generation unit 25, an output unit 26, a transmission control circuit 27, a control unit 28, and a tip position detection unit 29. The ultrasound unit 12 typically includes, for example, a processor, a memory, and a bus. A program related to, for example, a color Doppler signal generation process, a photoacoustic image generation process, an ultrasound image generation process, and a process of detecting the position of the tip of the puncture needle 15 in a photoacoustic image is incorporated into a memory in the ultrasound unit 12. The program is executed by the control unit 28 which is formed by a processor to implement the functions of the data demultiplexing unit 22, the color Doppler signal generation unit 23, the photoacoustic image generation unit 24, the ultrasound image generation unit 25, the output unit 26, and the tip position detection unit 29. That is, each of these units is formed by the processor and the memory into which the program has been incorporated.

The hardware configuration of the ultrasound unit 12 is not particularly limited and can be implemented by an appropriate combination of, for example, a plurality of integrated circuits (ICs), a processor, an application specific integrated circuit (ASIC), a field-programmable gate array (FPGA), and a memory.

The receiving circuit 20 receives a detection signal output from the ultrasound probe 11 and stores the received detection signal in the receiving memory 21. The receiving circuit 20 typically includes a low-noise amplifier, a variable-gain amplifier, a low-pass filter, and an analog-to-digital converter (AD converter). The detection signal of the ultrasound probe 11 is amplified by the low-noise amplifier. Then, gain adjustment corresponding to a depth is performed by the variable-gain amplifier and a high-frequency component of the detection signal is cut by the low-pass filter. Then, the detection signal is converted into a digital signal by the AD convertor and the digital signal is stored in the receiving memory 21. The receiving circuit 20 is formed by, for example, one integral circuit (IC).

The ultrasound probe 11 outputs a detection signal of the photoacoustic waves and a detection signal of the reflected ultrasonic waves. The AD-converted detection signals (sampling data) of the photoacoustic waves and the reflected ultrasonic waves are stored in the receiving memory 21.

In a case in which a photoacoustic image is generated, the data demultiplexing unit 22 reads the detection signal of the photoacoustic waves from the receiving memory 21 and transmits the detection signal to the photoacoustic image generation unit 24. In addition, in a case in which an ultrasound image is generated, the data demultiplexing unit 22 reads the detection signal of the reflected ultrasonic waves from the receiving memory 21 and transmits the detection signal to the ultrasound image generation unit 25. Further, in a case in which color Doppler measurement is performed, the data demultiplexing unit 22 reads a detection signal of reflected ultrasonic waves from an region of interest (hereinafter, referred to as an ROI) which is a color Doppler measurement target set by the control unit 28 and transmits the detection signal to the color Doppler signal generation unit 23.

The color Doppler signal generation unit 23 analyzes Doppler transition in the ROI on the basis of the detection signal of the reflected ultrasonic waves generated by the transmission of the pulsed ultrasonic waves to generate a color Doppler signal obtained by two-dimensionally mapping a distribution of a blood flow rate.

The photoacoustic image generation unit 24 generates a photoacoustic image on the basis of the detection signal of the photoacoustic waves detected by the ultrasound probe 11. The photoacoustic image generation process includes, for example, image reconfiguration, such as phasing addition, detection, and logarithmic conversion.

The ultrasound image generation unit 25 (corresponding to a reflected acoustic image generation unit according to the invention) generates an ultrasound image (reflected acoustic image) on the basis of the detection signal of the reflected ultrasonic waves detected by the ultrasound probe 11. The ultrasound image generation process includes image reconfiguration, such as phasing addition, detection, and logarithmic conversion.

The output unit 26 displays the photoacoustic image and the ultrasound image on a display unit 30 such as a display device. In addition, the output unit 26 displays a color Doppler image obtained by two-dimensionally mapping the distribution of the blood flow rate on the display unit 30 on the basis of the color Doppler signal. Further, the ultrasound image and the color Doppler image may be displayed so as to be superimposed on each other. Furthermore, a photoacoustic image may be displayed so as be superimposed on the ultrasound image and the color Doppler image.

The tip position detection unit 29 detects the position of the tip portion of the puncture needle 15 on the basis of the photoacoustic image generated by the photoacoustic image generation unit 24. As a method for detecting the position of the tip portion of the puncture needle 15, any method may be used as long as it can detect the position of a maximum brightness point in the photoacoustic image as the position of the tip portion of the puncture needle 15.

In a case in which the position of the tip of the puncture needle 15 is detected on the basis of the photoacoustic image as described above, in practice, an artifact of light or an artifact of sound is generated and a photoacoustic image in which photoacoustic waves are detected from a plurality of positions is likely to be generated and the original position of the tip portion of the puncture needle 15 is unlikely to be specified.

For this reason, the photoacoustic image generated by the photoacoustic image generation unit 24 is not used as it is, but, for example, a smoothing process may be performed for the photoacoustic image to prevent erroneous detection caused by the artifact. Specifically, the smoothing process is performed for the photoacoustic image subjected to detection and logarithmic conversion. For example, a filtering process using a Gaussian filter can be used as the smoothing process. It is preferable that the size of the Gaussian filter is less than that of the tip portion of the puncture needle 15.

Then, a binarization process is performed for the photoacoustic image subjected to the smoothing process to generate a binary image. Then, a region in which white pixels are continuously distributed is detected from the binary image to detect the position of the tip portion of the puncture needle 15. In this way, it is possible to detect the position of the tip portion of the puncture needle 15 with higher accuracy.

The control unit 28 controls each component in the ultrasound unit 12. For example, in a case in which a photoacoustic image is acquired, the control unit 28 transmits a trigger signal to the laser unit 13 such that the laser unit 13 emits pulsed laser light. In addition, the control unit 28 transmits a sampling trigger signal to the receiving circuit 20 to control, for example, the sampling start time of the photoacoustic waves with the emission of the laser light. The detection signal of the photoacoustic waves which has been received by the receiving circuit 20 and then converted into a digital signal is stored in the receiving memory 21.

In a case in which an ultrasound image is acquired, the control unit 28 transmits an ultrasound transmission trigger signal for commanding the transmission of ultrasonic waves to the transmission control circuit 27. In a case in which the ultrasound transmission trigger signal is received, the transmission control circuit 27 directs the ultrasound probe 11 to transmit ultrasonic waves. The control unit 28 transmits the sampling trigger signal to the receiving circuit 20 according to the transmission time of ultrasonic waves such that the receiving circuit 20 starts the sampling of the reflected ultrasonic waves. The detection signal of the ultrasonic waves which has been received by the receiving circuit 20 and then converted into a digital signal is stored in the receiving memory 21.

In a case in which color Doppler measurement is performed, the control unit 28 transmits a pulsed ultrasound transmission trigger signal for commanding the transmission of pulsed ultrasonic waves to the transmission control circuit 27. In a case in which the pulsed ultrasound transmission trigger signal is received, the transmission control circuit 27 directs the ultrasound probe 11 to transmit pulsed ultrasonic waves. The control unit 28 transmits the sampling trigger signal to the receiving circuit 20 according to the transmission time of pulsed ultrasonic waves such that the receiving circuit 20 starts the sampling of the reflected ultrasonic waves. The detection signal of the ultrasonic waves which has been received by the receiving circuit 20 and then converted into a digital signal is stored in the receiving memory 21.

In addition, in a case in which color Doppler measurement is performed, the control unit 28 sets an ROI which is a color Doppler measurement target. The color Doppler signal generation unit 23 generates a color Doppler signal on the basis of the ROI set by the control unit 28.

Here, in a case in which needling is performed with the puncture needle 15 having the photoacoustic wave generation portion 15*c* as described above and color Doppler measurement is performed by a color Doppler method, if the positional relationship between the tip of the puncture needle 15 and the ROI is not appropriately set, a signal caused by reflected waves from the puncture needle 15 is included as an artifact in the detection signal of the reflected ultrasonic waves in the color Doppler measurement, which makes it difficult to acquire an accurate color Doppler signal.

Figure 3:
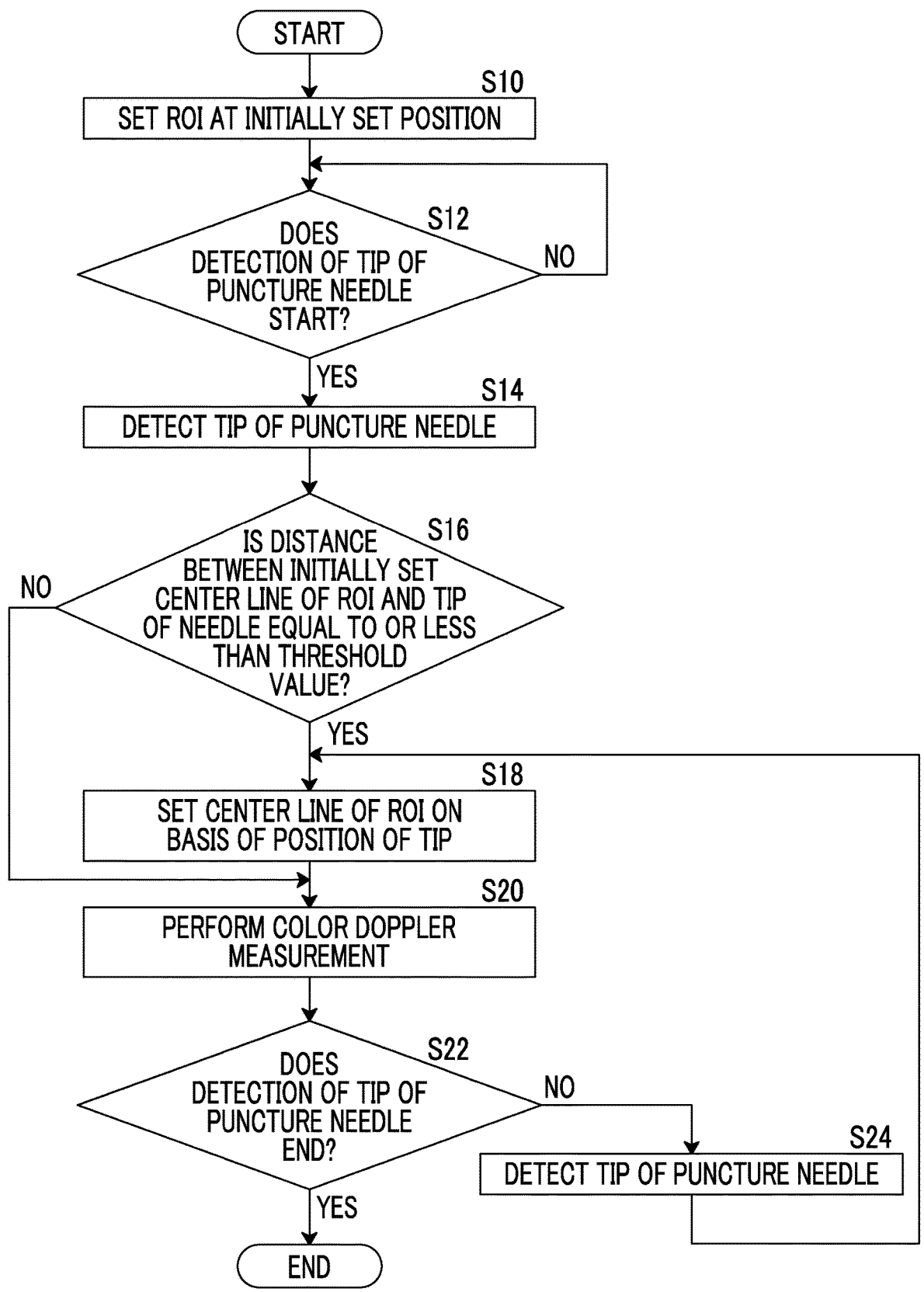
FIG. 3 is a flowchart illustrating a method for setting a region of interest in the photoacoustic image generation apparatus according to the first embodiment.

For this reason, the control unit 28 according to this embodiment sets the ROI at an appropriate position in order to suppress the generation of the artifact. Hereinafter, an ROI setting method by the control unit 28 will be described with reference to a flowchart illustrated in FIG. 3 and FIG. 4.

First, the control unit 28 sets the ROI at an initially set position (S10). The initially set position of the ROI may be stored in advance or the positional information of the ROI may be set and input by the user, such as a doctor, through an input unit 40 (see FIG. 1). In addition, an ultrasound image may be displayed on the display unit 30 (see FIG. 1) such that the user sets and inputs the initially set position of the ROI in the ultrasound image with the input unit 40. In addition, the initially set position of the ROI is set to a position where a blood vessel is assumed to be present in the subject M.

Then, the control unit 28 checks whether the user has input a command to start the detection of the tip of the puncture needle 15. In a case in which the tip detection start command has been input (S12, YES), the control unit 28 starts a process of detecting the position of the tip portion of the puncture needle 15 (S14). In addition, the user inputs the tip detection start command and a tip detection end command with the input unit 40 (see FIG. 1).

The detection signal of the photoacoustic waves detected by the ultrasound probe 11 is received by the receiving circuit 20 and is stored in the receiving memory 21 under the control of the control unit 28. Then, the data demultiplexing unit 22 transmits the detection signal of the photoacoustic waves from the receiving memory 21 to the photoacoustic image generation unit 24 and the photoacoustic image generation unit 24 generates a photoacoustic image of one frame.

The photoacoustic image of one frame generated by the photoacoustic image generation unit 24 is input to the tip position detection unit 29. The tip position detection unit 29 detects the position of the tip portion of the puncture needle 15.

Figure 4:
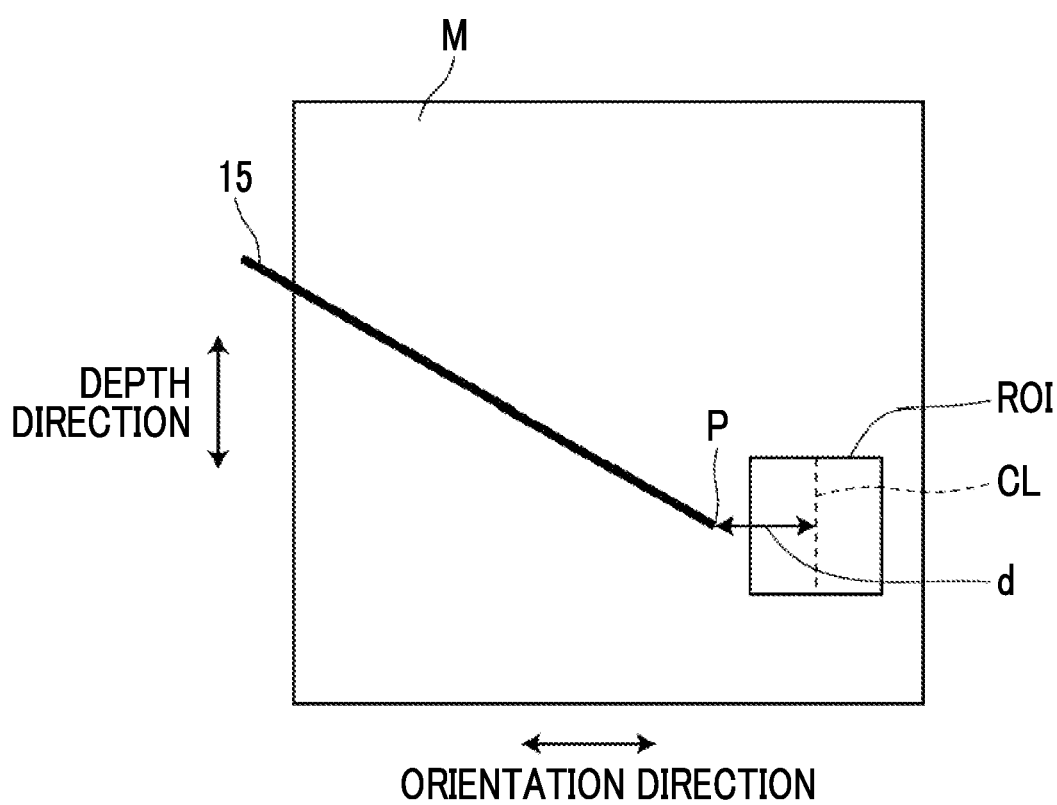
FIG. 4 is a diagram illustrating the method for setting the region of interest in the photoacoustic image generation apparatus according to the first embodiment.

Then, the positional information of the tip portion detected by the tip position detection unit 29 is input to the control unit 28. As illustrated in FIG. 4, the control unit 28 calculates a distance d between the position of a tip portion P of the puncture needle 15 and a center line CL of the ROI which has been initially set in an orientation direction and checks whether the distance d is equal to or less than a predetermined threshold value (S16). Then, in a case in which the distance d is greater than the predetermined threshold value (S16, NO), the control unit 28 determines that the positional relationship between the position of the tip portion P of the puncture needle 15 and the initially set position of the ROI is appropriate and performs color Doppler measurement at the initially set position of the ROI (S20). In this embodiment, it is assumed that the threshold value is equal to or greater than half of the length of the ROI in the orientation direction.

The orientation direction is, for example, a direction perpendicular to a depth direction in a case in which the ultrasound probe 11 is a linear type as illustrated in FIG. 4.

Specifically, the ultrasound probe 11 transmits pulsed ultrasonic waves. Then, the ultrasound probe 11 detects reflected ultrasonic waves generated by the transmission of the pulsed waves. Then, a detection signal of the reflected ultrasonic waves is received by the receiving circuit 20 and is stored in the receiving memory 21. Then, the data demultiplexing unit 22 transmits the detection signal of the reflected ultrasonic waves from the receiving memory 21 to the color Doppler signal generation unit 23. The color Doppler signal generation unit 23 generates a color Doppler signal on the basis of the initially set information of the ROI. Then, the output unit 26 displays a color Doppler image based on the color Doppler signal on the display unit 30.

On the other hand, in a case in which the distance d is equal to or less than the threshold value in S16 (S16, YES), the control unit 28 sets the center line CL of the ROI on the basis of the detected positional information of the tip portion P of the puncture needle 15 (S18). Specifically, the control unit 28 sets the center line CL of the ROI such that the distance d between the position of the tip portion P of the puncture needle 15 and the center line CL of the ROI is equal to the threshold value. Then, after the position of the ROI is set, color Doppler measurement is performed in the same way as described above (S20). In addition, in this embodiment, it is assumed that the position of the ROI in the depth direction is the initially set position of the ROI in the depth direction. Further, it is assumed that the width of the ROI in the orientation direction does not change. That is, in a case in which the center line CL of the ROI is set as described above, the ROI moves in parallel to the orientation direction according to the position of the tip portion P of the puncture needle 15 while maintaining the width in the orientation direction.

Then, the control unit 28 checks whether the user has input a command to end the detection of the tip of the puncture needle 15 (S22). In a case in which the tip detection end command has not been input (S22, NO), the control unit 28 detects the position of the tip portion P of the puncture needle 15 on the basis of a photoacoustic image of the next frame (S24). Then, the control unit 28 sets the center line CL of the ROI on the basis of the position of the tip portion P of the puncture needle 15 in the photoacoustic image of the next frame (S18). Specifically, similarly to the above, the control unit 28 sets the center line CL of the ROI such that the distance d between the position of the tip portion P of the puncture needle 15 and the center line CL of the ROI is equal to the threshold value. Then, after the position of the ROI is set, the control unit 28 performs color Doppler measurement in the same way as described above (S20).

Then, in S22, the control unit 28 repeatedly performs the detection of the tip of the puncture needle in S24, the setting of the center line CL of the ROI in S18, and the color Doppler measurement in S20 until the user inputs a command to end the detection of the tip of the puncture needle 15. The control unit 28 performs this process to set the center line CL of the ROI, following the movement of the tip portion of the puncture needle 15, in a state in which the distance d between the position of the tip portion P of the puncture needle 15 and the center line CL of the ROI is maintained at the threshold value.

Then, in a case in which the tip detection end command is input in S22 (S22, YES), the control unit 28 ends the process.

The photoacoustic image generation apparatus 10 according to the first embodiment generates a photoacoustic image on the basis of the detection signal of the photoacoustic waves generated from the photoacoustic wave generation portion 15c of the puncture needle 15, detects the position of the tip portion of the puncture needle 15 on the basis of the photoacoustic image, sets the center line CL of the ROI which is a color Doppler measurement target at a position that is a predetermined distance away from the detected position of the tip portion of the puncture needle 15, and sets the center line CL of the ROI, following the movement of the tip portion of the puncture needle 15, in a state in which the distance is maintained. Therefore, it is possible to always ensure the distance between the tip portion of the puncture needle 15 and the center line CL of the ROI and thus to suppress the generation of an artifact caused by the reflected waves from the puncture needle 15.

In the above-described embodiment, the threshold value of the distance d is equal to or greater than half of the length of the ROI in the orientation direction. However, the threshold value may be equal to half of the length of the ROI in the orientation direction. That is, in a case in which the orientation direction is the left-right direction, the center line CL of the ROI may be set such that the position of one end, which is closer to the tip portion of the puncture needle 15, of the left and right ends of a rectangular ROI in the left-right direction is matched with the position of the tip of the puncture needle 15 in the left-right direction. This setting of the threshold value makes it possible to always locate the left end or the right end of the ROI at the tip of the puncture needle 15, following the movement of the tip portion of the puncture needle 15.

In addition, the position of the tip of the puncture needle 15 in the left-right direction may not be necessarily matched with the left end or the right end of the ROI as described above. The center line CL of the ROI may be set such that the tip of the puncture needle 15 is included in a predetermined range from the position of the left end or the right end, considering, for example, an error in the detection of the tip of the puncture needle 15.

Figure 5:
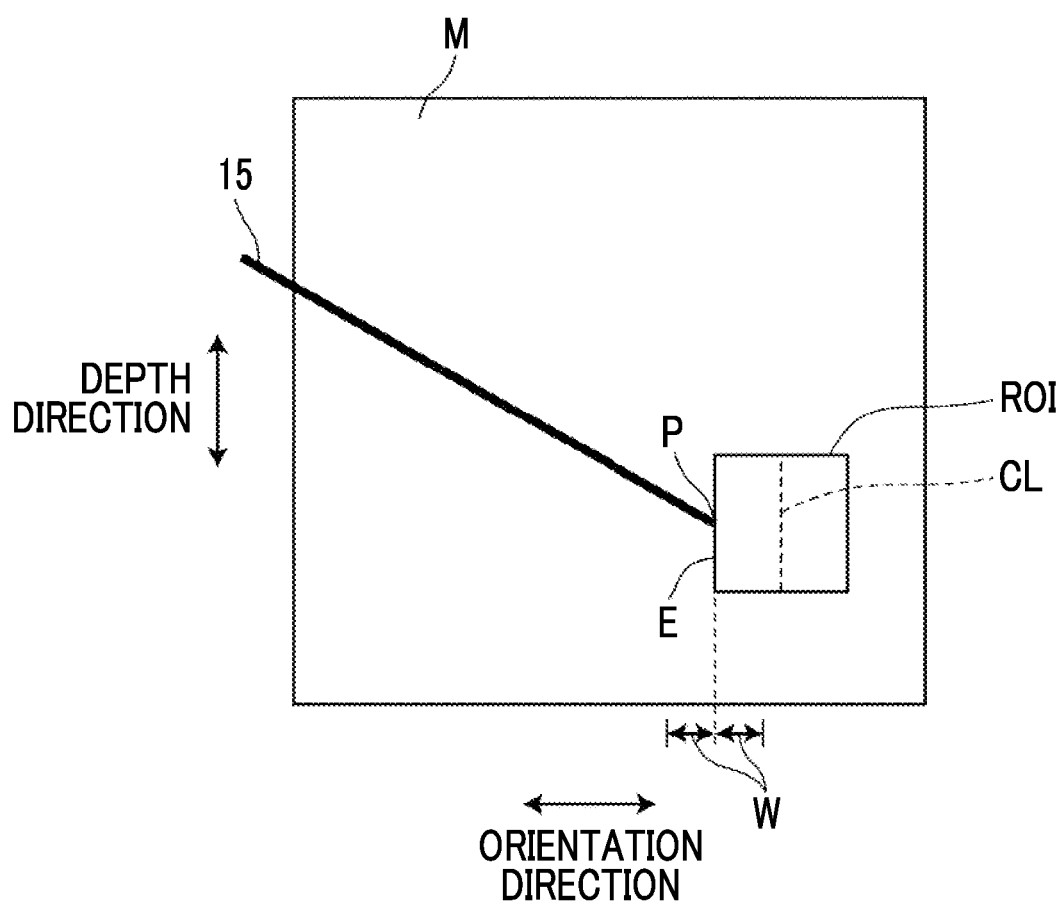
FIG. 5 is a diagram illustrating another method for setting the region of interest.

Specifically, for example, as illustrated in FIG. 5, the center line CL of the ROI may be set such that the tip of the puncture needle is included in a range of a width W in the left direction and the right direction from the position of a left end E of the ROI as a center line. It is preferable that the width W is set to, for example, the length of one ultrasound transducer (corresponding to a detection element according to the invention) of the ultrasound probe 11 in the orientation direction (left-right direction). However, the invention is not limited thereto. The width W may be set to a length that is 5% of the length of the ROI in the orientation direction (left-right direction).

In the first embodiment, in a case in which the position of the ROI is set such that the position of the tip of the puncture needle 15 and the center position of the ROI are separated from each other by a predetermined distance, the center line CL is used as an example of the center position. However, the center position is not limited to the center line CL. For example, any position, such as the left end or the right end of the ROI or one of four corners of the ROI, may be used as long as it can specify the position of the ROI.

Next, a second embodiment of the photoacoustic image generation apparatus according to the invention will be described. In the photoacoustic image generation apparatus 10 according to the first embodiment, in a case in which the position of the ROI is set on the basis of the position of the tip portion of the puncture needle 15, the position of the ROI in the depth direction is the initially set position of the ROI in the depth direction. However, a photoacoustic image generation apparatus 10 according to the second embodiment controls the position of the ROI in the depth direction.

Figure 6:
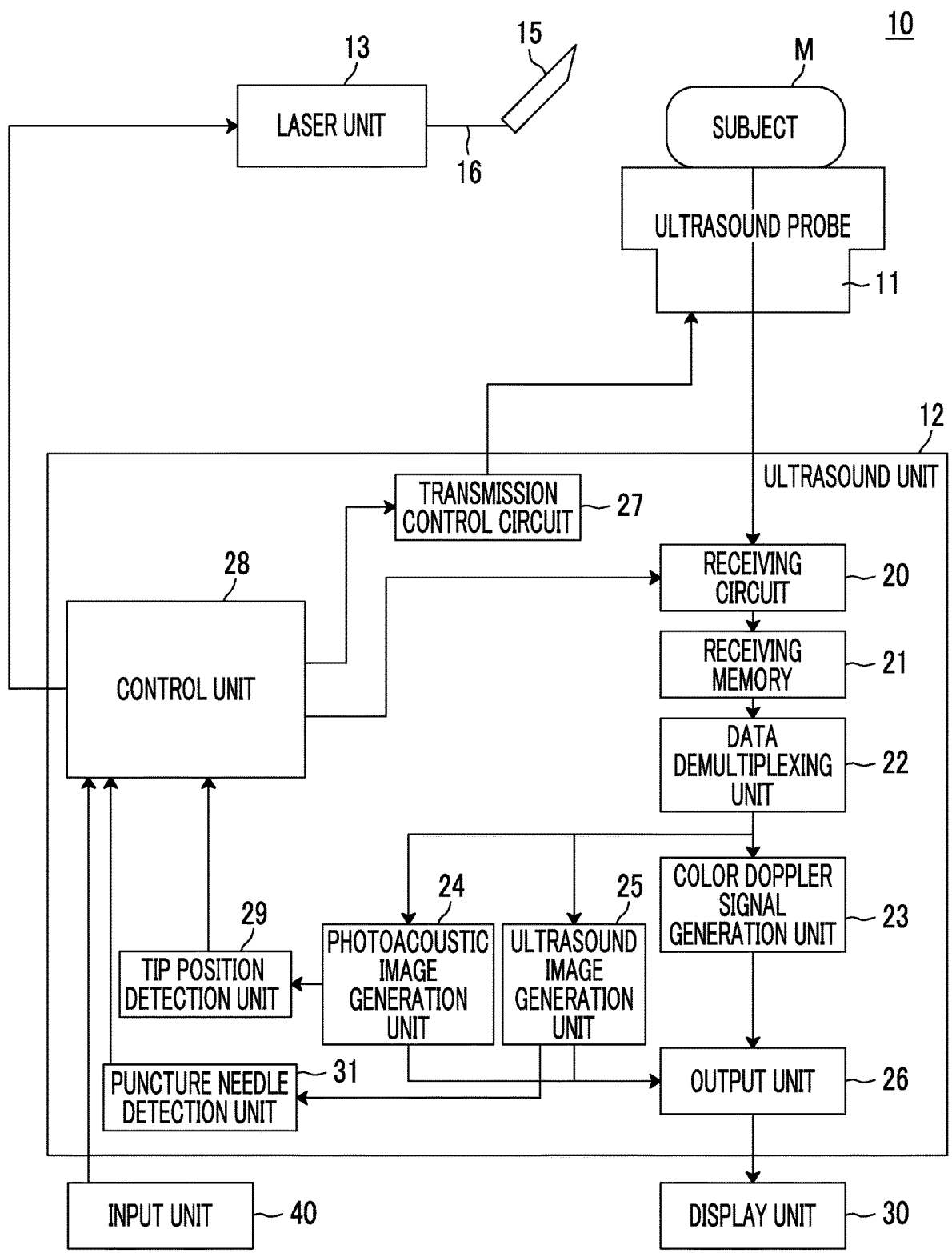
FIG. 6 is a block diagram schematically illustrating the configuration of a second embodiment of the photoacoustic image generation apparatus according to the invention.

FIG. 6 is a block diagram illustrating the configuration of the photoacoustic image generation apparatus 10 according to the second embodiment. As illustrated in FIG. 6, the photoacoustic image generation apparatus 10 according to the second embodiment differs from the photoacoustic image generation apparatus 10 according to the first embodiment in that it further comprises a puncture needle detection unit 31 (corresponding to an insert detection unit according to the invention). The other configurations are the same as those in the photoacoustic image generation apparatus 10 according to the first embodiment.

The puncture needle detection unit 31 detects an image of the puncture needle 15 from an ultrasound image on the basis of the ultrasound image generated by the ultrasound image generation unit 25 and detects a length direction of the puncture needle 15 on the basis of the image. As a method for detecting the image of the puncture needle 15, for example, a binarization process may be performed for the ultrasound image and a region in which white pixels are continuously arranged may be detected as an image region of the puncture needle 15. In addition, the invention is not limited to the method and the image of the puncture needle 15 may be detected by other known types of image processing.

Next, an ROI setting method in the photoacoustic image generation apparatus 10 according to the second embodiment will be described with reference to a flowchart illustrated in FIG. 7 and FIG. 8.

In the photoacoustic image generation apparatus 10 according to the second embodiment, first, the control unit 28 sets an ROI at the initially set position (S30). A method for setting the initially set position of the ROI is the same as that in the first embodiment.

Then, the control unit 28 checks whether the user has input a command to start the detection of the tip of the puncture needle 15. In a case in which the tip detection start command has been input (S32, YES), the control unit 28 starts a process of detecting the position of the tip portion of the puncture needle 15 (S34). In addition, the control unit 28 starts the transmission of ultrasonic waves for generating an ultrasound image at the same time as the start of the detection of the tip. In this embodiment, it is assumed that the emission of photoacoustic waves for the tip detection process and the transmission of ultrasonic waves for generating an ultrasound image are performed at the same frame interval.

Then, a detection signal of photoacoustic waves detected by the ultrasound probe 11 is received by the receiving circuit 20 and is stored in the receiving memory 21. Then, the data demultiplexing unit 22 transmits the detection signal of the photoacoustic waves from the receiving memory 21 to the photoacoustic image generation unit 24 and the photoacoustic image generation unit 24 generates a photoacoustic image of one frame.

The photoacoustic image of one frame generated by the photoacoustic image generation unit 24 is input to the tip position detection unit 29 and the tip position detection unit 29 detects the position of the tip portion of the puncture needle 15.

Figure 8:
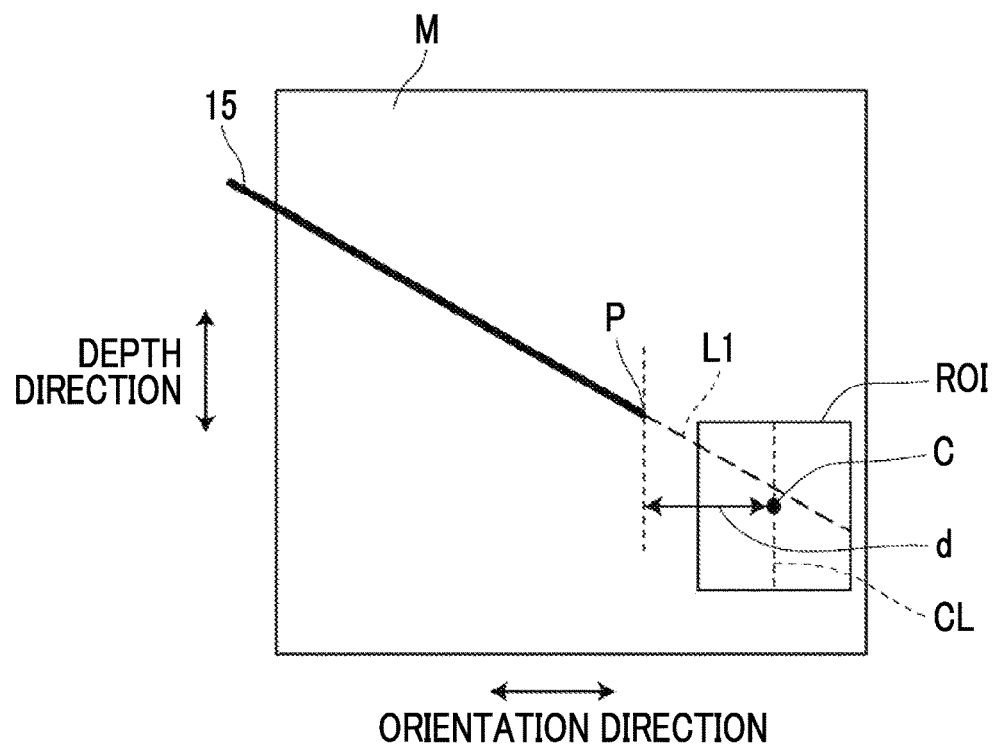
FIG. 8 is a diagram illustrating the method for setting the region of interest in the photoacoustic image generation apparatus according to the second embodiment.

The positional information of the tip portion detected by the tip position detection unit 29 is input to the control unit 28 and the control unit 28 calculates a distance d between the position of the tip portion P of the puncture needle 15 and the center line CL of the ROI which has been initially set in the orientation direction, as illustrated in FIG. 8, and checks whether the distance d is equal to or less than a predetermined threshold value (S36). Then, in a case in which the distance d is greater than the threshold value (S36, NO), the control unit 28 determines that the positional relationship between the position of the tip portion P of the puncture needle 15 and the center line CL of the ROI which has been initially set is appropriate and performs color Doppler measurement at the initially set position of the ROI (S42). Specifically, the ultrasound probe 11 transmits pulsed ultrasonic waves. Then, the ultrasound probe 11 detects reflected ultrasonic waves generated by the transmission of the pulsed waves. In addition, the transmission of pulsed waves for color Doppler measurement and the transmission of ultrasonic waves for generating an ultrasound image are performed at different times.

Then, a detection signal of the reflected ultrasonic waves generated by the transmission of the pulsed waves is received by the receiving circuit 20 and is stored in the receiving memory 21. Then, the data demultiplexing unit 22 transmits the detection signal of the reflected ultrasonic waves from the receiving memory 21 to the color Doppler signal generation unit 23. The color Doppler signal generation unit 23 generates a color Doppler signal on the basis of the initially set information of the ROI. Then, the output unit 26 displays a color Doppler image based on the color Doppler signal on the display unit 30.

On the other hand, in a case in which the distance d is equal to or less than the threshold value in S36 (S36, YES), a detection signal of the reflected ultrasonic waves detected by the ultrasound probe 11 is received by the receiving circuit 20 and is stored in the receiving memory 21. Then, the data demultiplexing unit 22 transmits the detection signal of the reflected ultrasonic waves from the receiving memory 21 to the ultrasound image generation unit 25 and the ultrasound image generation unit 25 generates an ultrasound image. The ultrasound image generated by the ultrasound image generation unit 25 is output to the puncture needle detection unit 31 and the puncture needle detection unit 31 detects the length direction of the puncture needle 15 from the input ultrasound image (S38).

The length direction of the puncture needle 15 detected by the puncture needle detection unit 31 is output to the control unit 28. The control unit 28 sets the center position of the ROI on the basis of the positional information of the tip portion of the puncture needle 15 and the length direction of the puncture needle 15 (S40). Specifically, for the position of the ROI in the orientation direction, as illustrated in FIG. 8, the control unit 28 sets the position of the ROI in the orientation direction such that the distance d between the position of the tip portion P of the puncture needle 15 and the center line CL of the ROI is equal to the threshold value as in the first embodiment. In addition, for the position of the ROI in the depth direction, as illustrated in FIG. 8, the control unit 28 sets the center position C of the ROI such that the center line CL of the ROI in the orientation direction (left-right direction) and a straight line L1 that extends in the length direction of the puncture needle 15 intersect each other in the ROI. In this case, it is assumed that the width of the ROI in the depth direction does not change. That is, in a case in which the center position C of the ROI is set as described above, the ROI moves in parallel to the depth direction according to the position of the tip portion P of the puncture needle 15 while maintaining the width in the depth direction.

This configuration in which the ROI is set on the straight line L1 extending in the length direction of the puncture needle 15 makes it possible to rapidly check the blood flow rate of a blood vessel that is present in a traveling direction of the puncture needle 15. Then, after the ROI is set as described above, color Doppler measurement is performed in the same way as described above (S42).

Then, the control unit 28 checks whether the user has input a command to end the detection of the tip of the puncture needle 15. In a case in which the tip detection end command has not been input (S44, NO), the control unit 28 detects the position of the tip portion P of the puncture needle 15 on the basis of a photoacoustic image of the next frame (S46). Then, the puncture needle detection unit 31 detects the length direction of the puncture needle 15 on the basis of the ultrasound image of the next frame (S38). Then, the control unit 28 sets the center position C of the ROI on the basis of the position of the tip portion P of the puncture needle 15 in the photoacoustic image of the next frame and the length direction of the puncture needle 15 in the ultrasound image of the next frame in the same way as described above (S40). Then, after the center position C of the ROI is set, the control unit 28 performs color Doppler measurement in the same way as described above (S42).

Then, in S44, the control unit 28 repeatedly performs the detection of the tip of the puncture needle in S46, the detection of the length direction of the puncture needle in S38, the setting of the center position of the ROI in S40, and the color Doppler measurement in S42 until the user inputs a command to end the detection of the tip of the puncture needle 15. The control unit 28 performs this process to set the position of the ROI in the orientation direction, following the movement of the tip portion of the puncture needle 15, in a state in which the distance d between the position of the tip portion P of the puncture needle 15 and the center line CL of the ROI is maintained at the threshold value, and sets the position of the ROI in the depth direction in the traveling direction of the puncture needle 15.

Then, in a case in which the tip detection end command is input in S44 (S44, YES), the control unit 28 ends the process.

Figure 9:
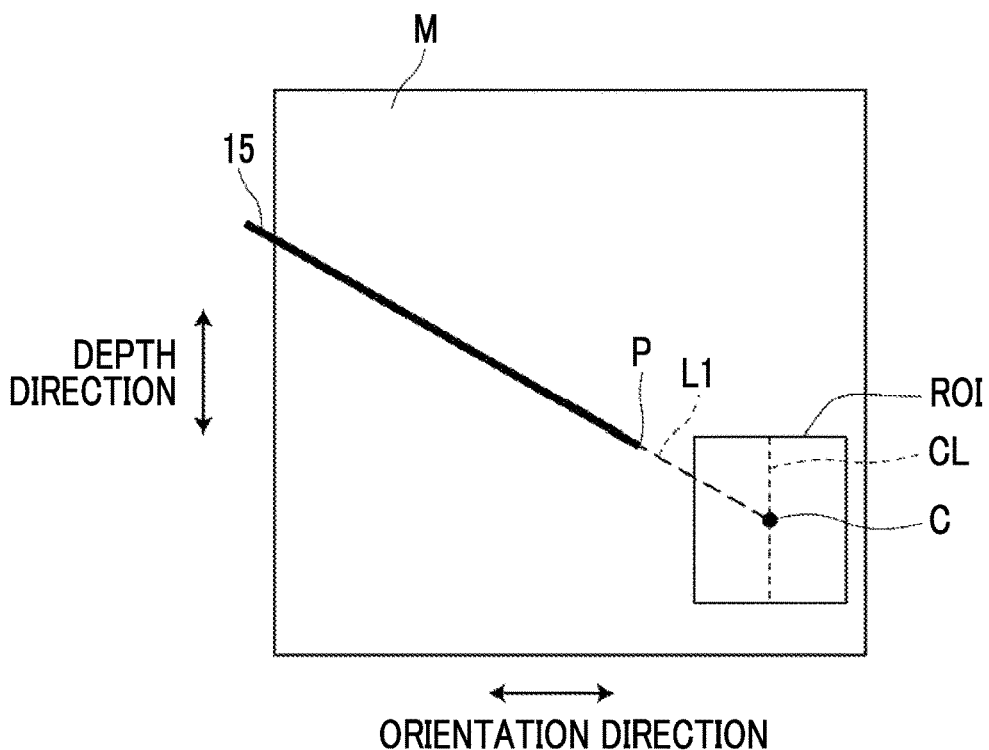
FIG. 9 is a diagram illustrating another method for setting the position of the region of interest in a depth direction.

The photoacoustic image generation apparatus 10 according to the second embodiment sets the center position C of the ROI such that the straight line L1 extending in the length direction of the puncture needle 15 and the center line CL of the ROI in the orientation direction (left-right direction) intersect each other in the ROI as illustrated in FIG. 8. However, the invention is not limited thereto. The position of the ROI in the depth direction may be set such that the straight line L1 extending in the length direction of the puncture needle 15 passes through the center position C of the ROI as illustrated in FIG. 9.

Figure 10:
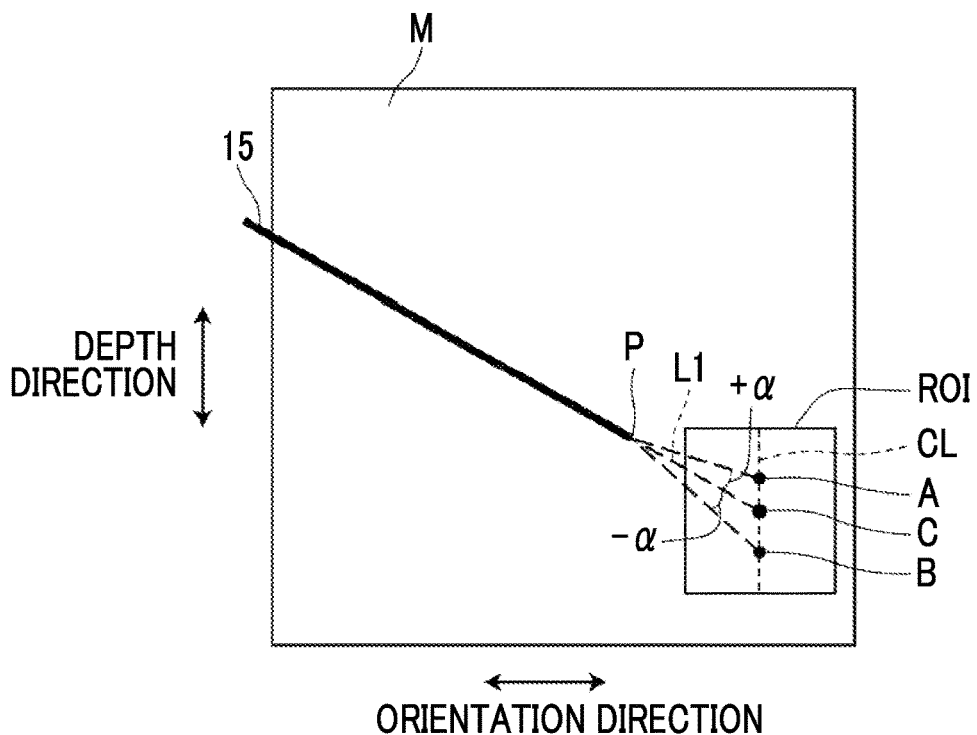
FIG. 10 is a diagram illustrating still another method for setting the position of the region of interest in the depth direction.

However, an error is likely to occur in the length direction of the puncture needle 15 depending on the accuracy of detecting the image of the puncture needle 15. Therefore, the position of the ROI in the depth direction may be set in consideration of the error in the length direction of the puncture needle 15. Specifically, the position of the ROI in the depth direction may be set such that the straight line L1 and the center line CL of the ROI intersect each other in a predetermined range from the center position C of the ROI in the depth direction. For example, as illustrated in FIG. 10, the predetermined range may be a range between a point A where the straight line L1 and the center line CL of the ROI intersect each other in a case in which the angle of the straight line L1 that passes through the center position C of the ROI and extends in the length direction of the puncture needle 15 is shifted by $+\alpha°$ and a point B where the center line CL of the ROI and the straight line L1 intersect each other in a case in which the angle is shifted by $-\alpha°$. The angle of $\pm\alpha$ is preferably set to a range of, for example, $\pm1°$ to $5°$.

In addition, in the photoacoustic image generation apparatus 10 according to the second embodiment, the position of the ROI in the depth direction is set as described above in terms of setting the ROI in the traveling direction of the puncture needle 15. However, the invention is not limited thereto. For example, the position of the ROI in the depth direction may be set in terms of minimizing the influence of the photoacoustic waves generated from the photoacoustic wave generation portion 15c of the puncture needle 15.

Figure 11:
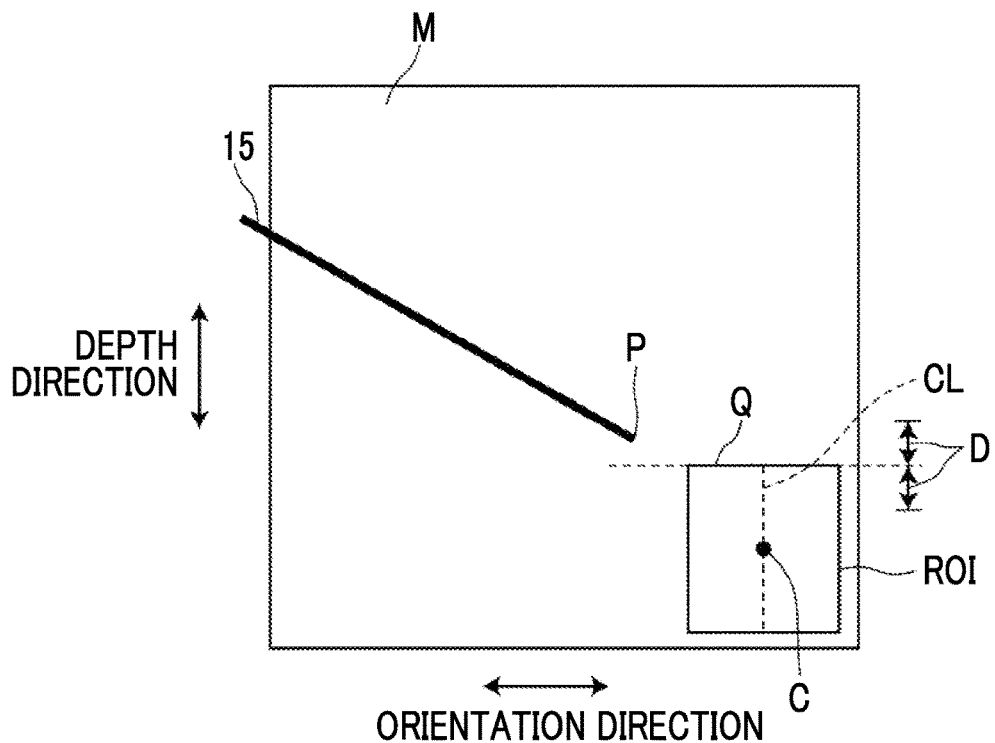
FIG. 11 is a diagram illustrating yet another method for setting the position of the region of interest in the depth direction.

Specifically, as illustrated in FIG. 11, in a case in which a side of the subject M in the depth direction which is close to the ultrasound probe 11 is the upper side, the center position C of the ROI may be set such that an upper end Q of the ROI is lower than the position of the tip portion P of the puncture needle 15. This setting of the position of the ROI in the depth direction makes it possible to minimize the influence of the photoacoustic waves generated from the photoacoustic wave generation portion 15c of the puncture needle 15.

In addition, the center position C of the ROI may be set such that the upper end Q of the ROI is matched with the position of the tip of the puncture needle 15 in the up-down direction. The upper end Q of the ROI may not be necessarily matched with the position of the tip of the puncture needle 15 in the up-down direction and the center position C of the ROI may be set such that the tip of the puncture needle 15 is included in a predetermined range from the position of the upper end Q of the ROI as a center line in the depth direction in consideration of an error in the detection of the tip of the puncture needle 15. Specifically, for example, as illustrated in FIG. 11, the center position C of the ROI may be set such that the tip of the puncture needle 15 is included in a range of a width D in the upper direction and the lower direction from the upper end Q of the ROI as a center line. The width D may be set to, for example, a length that is 5% of the length of the ROI in the depth direction (up-down direction).

Figure 7:
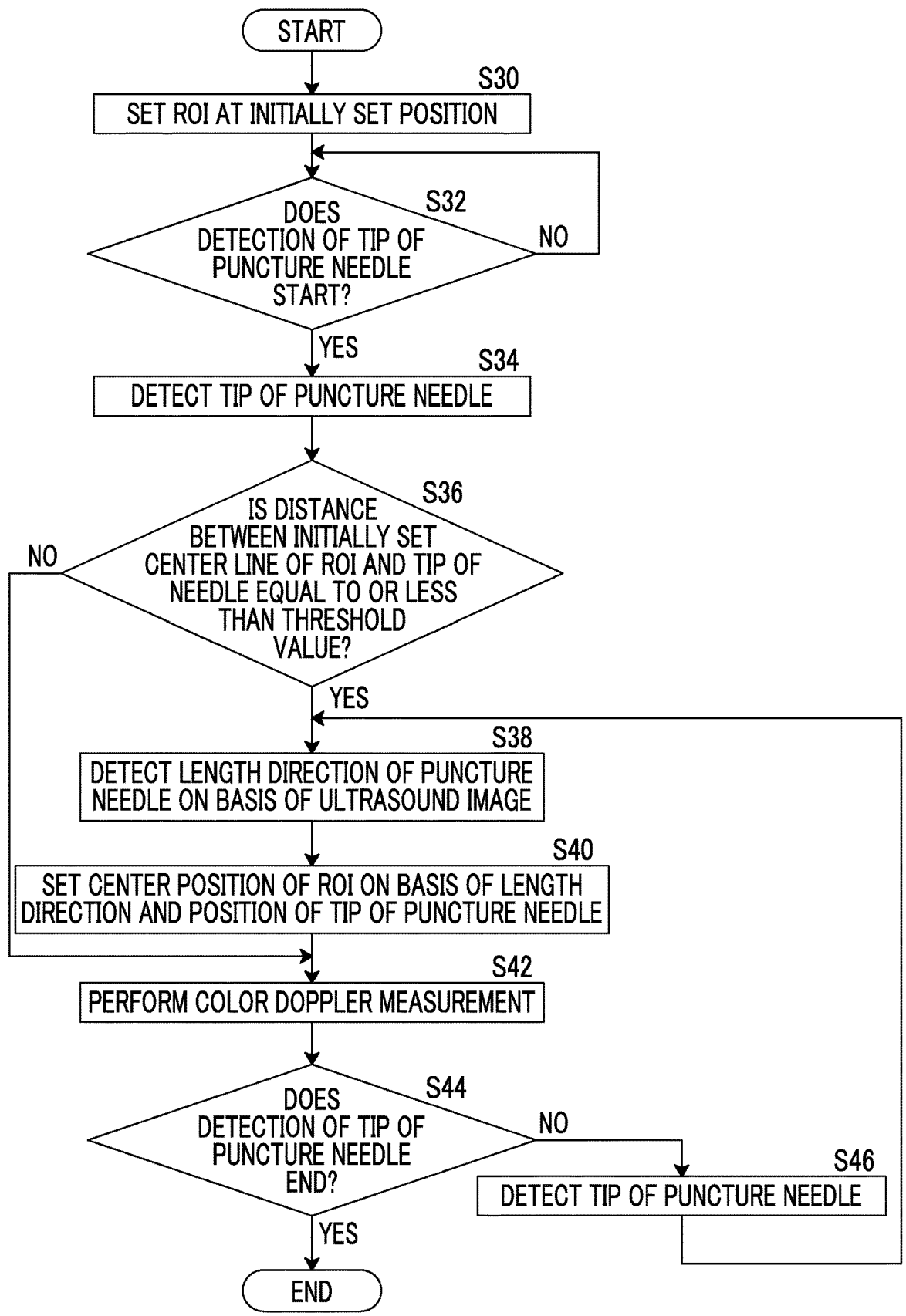
FIG. 7 is a flowchart illustrating a method for setting a region of interest in the photoacoustic image generation apparatus according to the second embodiment.

In the photoacoustic image generation apparatus 10 according to the second embodiment, after the distance between the center line CL of the ROI which has been initially set and the position of the tip portion of the puncture needle 15 is equal to or less than the threshold value in S36 illustrated in FIG. 7, an ultrasound image is acquired for each frame of the photoacoustic image and the length direction of the puncture needle 15 is detected on the basis of the ultrasound image. However, since the length direction of the puncture needle 15 is not frequently changed, it is not necessary to detect the length direction of the puncture needle 15 for each frame. Therefore, the length direction of the puncture needle 15 may be detected at each interval of two or more frames. In this case, it is possible to reduce the load of the detection process of the puncture needle 15.

In addition, the puncture needle detection unit 31 may acquire the amount of change in the angle of the length direction of the puncture needle 15 on the basis of the length direction of the puncture needle 15 and the frame interval at which the process of detecting the length direction of the puncture needle 15 is performed may be increased in a case in which the amount of change is equal to or less than a predetermined threshold value. In a case in which there is no change in the angle of the length direction of the puncture needle 15, the process of detecting the length direction of the puncture needle 15 may not be performed (may be omitted) for a reflected acoustic image of the next frame. FIG. 12 is a diagram illustrating an example of a case in which the timing of the process of detecting the length direction of the puncture needle 15 is controlled as described above. Here, the angle of the length direction of the puncture needle 15 means an acute angle among the angles formed between a straight line extending in the length direction of the puncture needle 15 and a straight line extending in the depth direction.

As illustrated in FIG. 12, in a second frame, there is no change in the angle of the length direction of the puncture needle 15 from a first frame. Therefore, in a third frame, the process of detecting the length direction of the puncture needle 15 is not performed. In a fourth frame, the process of detecting the length direction of the puncture needle 15 is performed again. However, since the angle has not been changed from the previously detected angle, the process of detecting the length direction of the puncture needle 15 is not performed in the fifth and sixth frames. That is, the frame interval at which the process of detecting the length direction of the puncture needle 15 is not performed is increased. Then, in a seventh frame, the process of detecting the length direction of the puncture needle 15 is performed again. However, since the angle has not been changed from the previously detected angle, the frame interval at which the process of detecting the length direction of the puncture needle 15 is not performed is further increased. That is, the process of detecting the length direction of the puncture needle 15 is not performed in three frames, that is, eighth to tenth frames.

Then, in an eleventh frame, the process of detecting the length direction of the puncture needle 15 is performed again. In the process of detecting the length direction of the puncture needle 15 for the eleventh frame, the angle has been changed from the previously detected angle. Therefore, in a twelfth frame, the process of detecting the length direction of the puncture needle 15 is also performed. In the process of detecting the length direction of the puncture needle 15 for the twelfth frame, the angle has been changed from the previously detected angle. Therefore, in a thirteenth frame, the process of detecting the length direction of the puncture needle 15 is also performed. In the process of detecting the length direction of the puncture needle 15 for the thirteenth frame, the angle has been changed from the previously detected angle. Therefore, in a fourteenth frame, the process of detecting the length direction of the puncture needle 15 is also performed. Since the angle has not been changed from the previously detected angle in the fourteenth frame, the process of detecting the length direction of the puncture needle 15 is not performed in a fifteenth frame. Then, in a sixteenth frame, the process of detecting the length direction of the puncture needle 15 is performed again. However, since the angle has not been changed from the previously detected angle, the process of detecting the length direction of the puncture needle 15 is not performed in seventeenth and eighteenth frames. Then, in a nineteenth frame, the process of detecting the length direction of the puncture needle 15 is performed again. However, since the angle has not been changed from the previously detected angle, the process of detecting the length direction of the puncture needle 15 is not performed in a twentieth frame.

Figure 13:
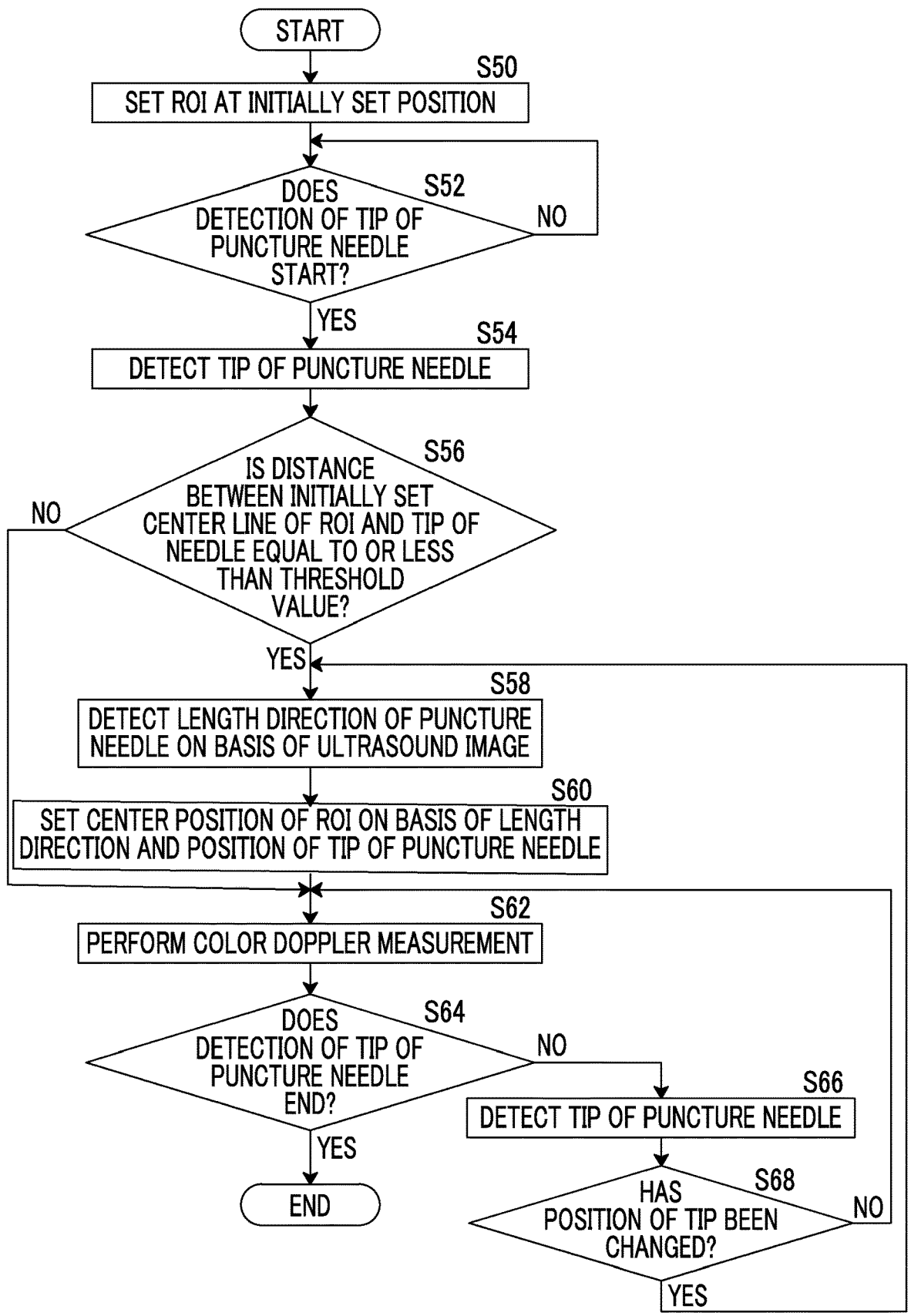
FIG. 13 is a flowchart illustrating a method for controlling the turn-on and turn-off of the process of detecting the length direction of the puncture needle on the basis of a change in the position of the tip portion of the puncture needle.

In the photoacoustic image generation apparatus 10 according to the second embodiment, in the process of detecting the position of the tip of the puncture needle 15, in a case in which the position of the tip of the puncture needle 15 has not been changed from the position of the tip in the photoacoustic image of the previous frame, the process of detecting the length direction of the puncture needle 15 and the process of setting the center position of the ROI on the basis of the position of the tip of the puncture needle 15 and the length direction of the puncture needle 15 may not be performed (may be omitted). FIG. 13 is a flowchart in this case.

In the flowchart illustrated in FIG. 13, a process in S50 and S52 and S54 to S62 based on an ultrasound image and a photoacoustic image of the initial frame is the same as that in the second embodiment.

Then, the tip of the puncture needle 15 is detected on the basis of the photoacoustic images of the second and subsequent frames (S66). At that time, in a case in which the position of the tip has not been changed from the position of the tip in the photoacoustic image of the previous frame (S68, NO), the process of detecting the length direction of the puncture needle 15 in S58 and the process of setting the center position of the ROI in S60 are not performed and color Doppler measurement is performed (S62). On the other hand, in a case in which the position of the tip has been changed from the position of the tip in the photoacoustic image of the previous frame in S68 (S68, YES), the process of detecting the length direction of the puncture needle 15 in S58 and the process of setting the center position C of the ROI in S60 are performed and then color Doppler measurement is performed (S62).

Then, in S64, the process in S66 to S68 and S58 to S62 is repeatedly performed until the user inputs a command to end the detection of the tip of the puncture needle 15. In a case in which the tip detection end command is input in S64 (S64, YES), the process ends.

In the second embodiment, the positional relationship between the tip of the puncture needle 15 and the ROI in the depth direction is controlled. However, the invention is not limited to the control method according to the second embodiment. For example, the position of the ROI may be controlled such that the distance between the tip of the puncture needle 15 and the center position C of the ROI is equal to or greater than a predetermined distance in the depth direction. Further, in an oblique direction in addition to the orientation direction and the depth direction which are orthogonal to each other, the position of the ROI may be controlled such that the distance between the tip of the puncture needle 15 and the center position C of the ROI is equal to or greater than a predetermined distance in the depth direction. For example, the predetermined distance may be set on the basis of the size of the ROI as in the above-described embodiments. Alternatively, the position of the ROI may be controlled such that the tip of the puncture needle 15 is located at a position that is separated outward from the end of the ROI by a predetermined distance.

In the second embodiment, in a case in which the position of the ROI is set such that the position of the tip of the puncture needle 15 and the center position of the ROI are separated from each other by a predetermined distance, the center position C of the ROI is used as an example. However, the position is not limited to the center position C. For example, any position, such as the upper end, the lower end, the left end, or the right end of the ROI or one of four corners of the ROI, may be used as long as it can specify the position of the ROI.

In the above-described embodiments, the puncture needle 15 is used as an embodiment of the insert. However, the invention is not limited thereto. The insert may be a radio-frequency ablation needle including an electrode that is used for radio-frequency ablation, a catheter that is inserted into a blood vessel, or a guide wire for a catheter that is inserted into a blood vessel. Alternatively, the insert may be an optical fiber for laser treatment.

The insert according to the invention is not limited to a needle, such as an injection needle, and may be a biopsy needle used for biopsy. That is, the needle may be a biopsy needle that is inserted into an inspection target of the living body and extracts the tissues of a biopsy site of the inspection target. In this case, photoacoustic waves may be generated from an extraction portion (intake port) for sucking and extracting the tissues of the biopsy site. In addition, the needle may be used as a guiding needle that is used for insertion into a deep part, such as a part under the skin or an organ inside the abdomen.

The invention has been described above on the basis of the preferred embodiments. However, the insert and the photoacoustic image generation apparatus according to the invention are not limited only to the above-described embodiments. Various modifications and changes of the configurations according to the above-described embodiments are also included in the scope of the invention.

What is claimed is:

1. A photoacoustic image generation apparatus comprising:
    an insert of which at least a tip portion is configured to be inserted into a subject and which includes a light guide member that guides light to the tip portion and a photoacoustic wave generation portion that absorbs the light guided by the light guide member and generates photoacoustic waves;
    an acoustic wave detection unit that detects the photoacoustic waves generated from the photoacoustic wave generation portion in a first scanning plane and detects reflected acoustic waves reflected by transmission of acoustic waves to the subject in the first scanning plane;
    a processor that generates a color Doppler signal on the basis of the reflected acoustic waves in a region of interest narrower than the first scanning plane within the first scanning plane as a color Doppler measurement target which have been detected by the acoustic wave detection unit, generates a photoacoustic image on the basis of the photoacoustic waves detected by the acoustic wave detection unit, and detects a position of the tip portion of the insert on the basis of the photoacoustic image; and
    a controller that sets the region of interest such that the position of the tip portion of the insert detected by the processor and a center position of the region of interest are separated from each other by a predetermined distance in the first scanning plane and sets the region of interest, following movement of the tip portion of the insert, in a state in which the distance is maintained, wherein
    the processor further generates a reflected acoustic image on the basis of the reflected acoustic waves and detects a length direction of the insert on the basis of the reflected acoustic image,
    the controller sets the region of interest such that a center line of the region of interest in an orientation direction and a straight line extending in the length direction of the insert intersect each other in the region of interest,
    the processor detects the length direction of the insert at each interval of two or more frames of the reflected acoustic image, and
    acquires an amount of change in an angle of the length direction of the insert and increases the frame interval at which the length direction of the insert is detected in a case in which the amount of change is equal to or less than a predetermined threshold value.

2. The photoacoustic image generation apparatus according to claim 1,
    wherein, in a case in which the orientation direction is a left-right direction, the controller sets the region of interest such that the tip portion of the insert is included in a predetermined range in the left-right direction from a position of one end, which is closer to the tip portion of the insert, of left and right ends of the region of interest having a rectangular shape.

3. The photoacoustic image generation apparatus according to claim 2,
    wherein a plurality of detection elements that detect the reflected acoustic waves and the photoacoustic waves are arranged in the acoustic wave detection unit, and
    the controller sets the center line of the region of interest in the left-right direction such that the tip portion of the insert is included in a range of a length of one detection element in the left-right direction from the position of the one end of the region of interest which is closer to the tip portion of the insert.

4. The photoacoustic image generation apparatus according to claim 2,
    wherein the controller sets the center line of the region of interest in the orientation direction such that the tip portion of the insert is included in a range of a length which is 5% of a length of the region of interest in the orientation direction from the position of the one end of the region of interest which is closer to the tip portion of the insert.

5. The photoacoustic image generation apparatus according to claim 2,
    wherein the controller sets the region of interest such that the position of the one end of the region of interest which is closer to the tip portion of the insert in the left-right direction is matched with the position of the tip portion of the insert in the left-right direction.

6. The photoacoustic image generation apparatus according to claim 1,
    wherein the controller sets the region of interest such that the center line of the region of interest in the orientation direction and the straight line extending in the length direction of the insert intersect each other in a predetermined range from the center position of the region of interest in a depth direction.

7. The photoacoustic image generation apparatus according to claim 1,
    wherein the controller sets the region of interest such that the straight line extending in the length direction of the insert intersects the center portion of the region of interest.

8. The photoacoustic image generation apparatus according to claim 1,
    wherein, in a case in which a side of the subject which the acoustic wave detection unit is placed in a depth direction is an upper side, the controller sets the region of interest such that the upper side of the region of interest having a rectangular shape is lower than the position of the tip portion of the insert.

9. The photoacoustic image generation apparatus according to claim 1,
    wherein, in a case in which a side of the subject which the acoustic wave detection unit is placed in a depth direction is an upper side, the controller sets the region of interest such that the tip portion of the insert is included in a predetermined range in an upper direction and a lower direction from a position of the upper side of the region of interest having a rectangular shape.

10. The photoacoustic image generation apparatus according to claim 9,
wherein the controller sets the center line of the region of interest in the depth direction such that the tip of the insert portion is included in a range of a length, which is 5% of a length of the region of interest in the depth direction, in each of the upper direction and the lower direction from the position of the upper side of the region of interest.

11. The photoacoustic image generation apparatus according to claim 1,
wherein, in a case in which a side of the subject which the acoustic wave detection unit is placed in a depth direction is an upper side, the controller sets the region of interest such that a position of the upper side of the region of interest in an up-down direction is matched with the position of the tip portion of the insert in the up-down direction.

12. The photoacoustic image generation apparatus according to claim 1,
wherein the insert is a needle that is configured to be inserted into the subject.

13. A photoacoustic image generation apparatus comprising:
an insert of which at least a tip portion is configured to be inserted into a subject and which includes a light guide member that guides light to the tip portion and a photoacoustic wave generation portion that absorbs the light guided by the light guide member and generates photoacoustic waves;
an acoustic wave detection unit that detects the photoacoustic waves generated from the photoacoustic wave generation portion in a first scanning plane and detects reflected acoustic waves reflected by transmission of acoustic waves to the subject in the first scanning plane;
a processor that generates a color Doppler signal on the basis of the reflected acoustic waves in a region of interest narrower than the first scanning plane within the first scanning plane as a color Doppler measurement target which have been detected by the acoustic wave detection unit, generates a photoacoustic image on the basis of the photoacoustic waves detected by the acoustic wave detection unit, and detects a position of the tip portion of the insert on the basis of the photoacoustic image; and
a controller that sets the region of interest such that the position of the tip portion of the insert detected by the processor and a center position of the region of interest are separated from each other by a predetermined distance in the first scanning plane and sets the region of interest, following movement of the tip portion of the insert, in a state in which the distance is maintained, wherein
the processor further generates a reflected acoustic image on the basis of the reflected acoustic waves and detects a length direction of the insert on the basis of the reflected acoustic image,
the controller sets the region of interest such that a center line of the region of interest in an orientation direction and a straight line extending in the length direction of the insert intersect each other in the region of interest, and
in a case in which the position of the tip portion of the insert detected by the processor is the same as a position of the tip portion of the insert in the photoacoustic image of a previous frame, the detection of the length direction of the insert based on the reflected acoustic image and the setting of the region of interest are not performed.

\* \* \* \* \*